United States Patent [19]

Yoon

[11] Patent Number: 5,292,310
[45] Date of Patent: Mar. 8, 1994

[54] SAFETY NEEDLE

[76] Inventor: InBae Yoon, 2101 Highland Ridge Dr., Phoenix, Md. 21131

[21] Appl. No.: 688,139

[22] Filed: Dec. 27, 1990

[51] Int. Cl.⁵ ............................................. A61M 5/178
[52] U.S. Cl. ................... 604/158; 604/272; 606/185; 128/753
[58] Field of Search ..................... 604/51-53, 604/158-163, 272-274, 283, 22, 26; 128/751-754; 606/184, 185, 171

[56] References Cited

U.S. PATENT DOCUMENTS

| | | | |
|---|---|---|---|
| 1,087,845 | 2/1914 | Stevens | 604/159 |
| 1,248,492 | 12/1917 | Hill | 604/165 |
| 1,527,291 | 2/1925 | Zorraquin . | |
| 2,389,355 | 11/1945 | Goland et al. . | |
| 2,496,111 | 1/1950 | Turkel . | |
| 2,623,521 | 12/1952 | Shaw . | |
| 2,630,803 | 3/1953 | Baran . | |
| 2,952,256 | 9/1960 | Meader et al. | 604/272 |
| 4,068,659 | 1/1978 | Moorehead | 604/53 |
| 4,144,884 | 3/1979 | Teresteegen et al. . | |
| 4,254,762 | 3/1981 | Yoon . | |
| 4,345,589 | 8/1982 | Hiltebrandt . | |
| 4,513,754 | 4/1985 | Lee | 128/753 |
| 4,535,773 | 8/1985 | Yoon . | |
| 4,627,841 | 12/1986 | Door . | |
| 4,630,616 | 12/1986 | Tretinyak | 128/753 |
| 4,654,030 | 3/1987 | Moll et al. . | |
| 4,808,170 | 2/1989 | Thorton et al. | 604/274 |
| 4,869,717 | 9/1989 | Adair . | |
| 4,995,866 | 2/1991 | Amplatz et al. | 604/53 |
| 5,226,426 | 7/1993 | Yoon | 606/185 |

FOREIGN PATENT DOCUMENTS

| | | | |
|---|---|---|---|
| 2544262 | 4/1977 | Fed. Rep. of Germany . | |
| 0878265 | 11/1981 | U.S.S.R. | 604/93 |
| 1435246 | 11/1984 | U.S.S.R. . | |
| 0904635 | 8/1962 | United Kingdom | 604/158 |

Primary Examiner—C. Fred Rosenbaum
Assistant Examiner—Mark Bockelman

[57] ABSTRACT

A safety needle includes an elongate tubular needle and safety probe movable therein between an extended position with a blunt distal end of the safety probe projecting distally of the needle distal end and a retracted position with the safety probe distal end disposed proximally of the needle distal end. In one embodiment, the safety probe forms a protective recess for receiving the sharp tip of the needle in the extended position. In another embodiment, the needle distal end has a peripheral edge disposed in a plane positioned at an acute angle relative to the longitudinal axis of the needle, and the safety probe has a distal end surface disposed in substantially the same plane as the distal end of the needle during penetration through tissue. In a further embodiment, the needle has a portion curving toward the longitudinal axis of the needle to terminate at the sharp tip. A pin and slot locking mechanism allows selective, releasable locking of the safety probe in the retracted and/or extended positions and manual movement of the safety probe in the needle.

9 Claims, 2 Drawing Sheets

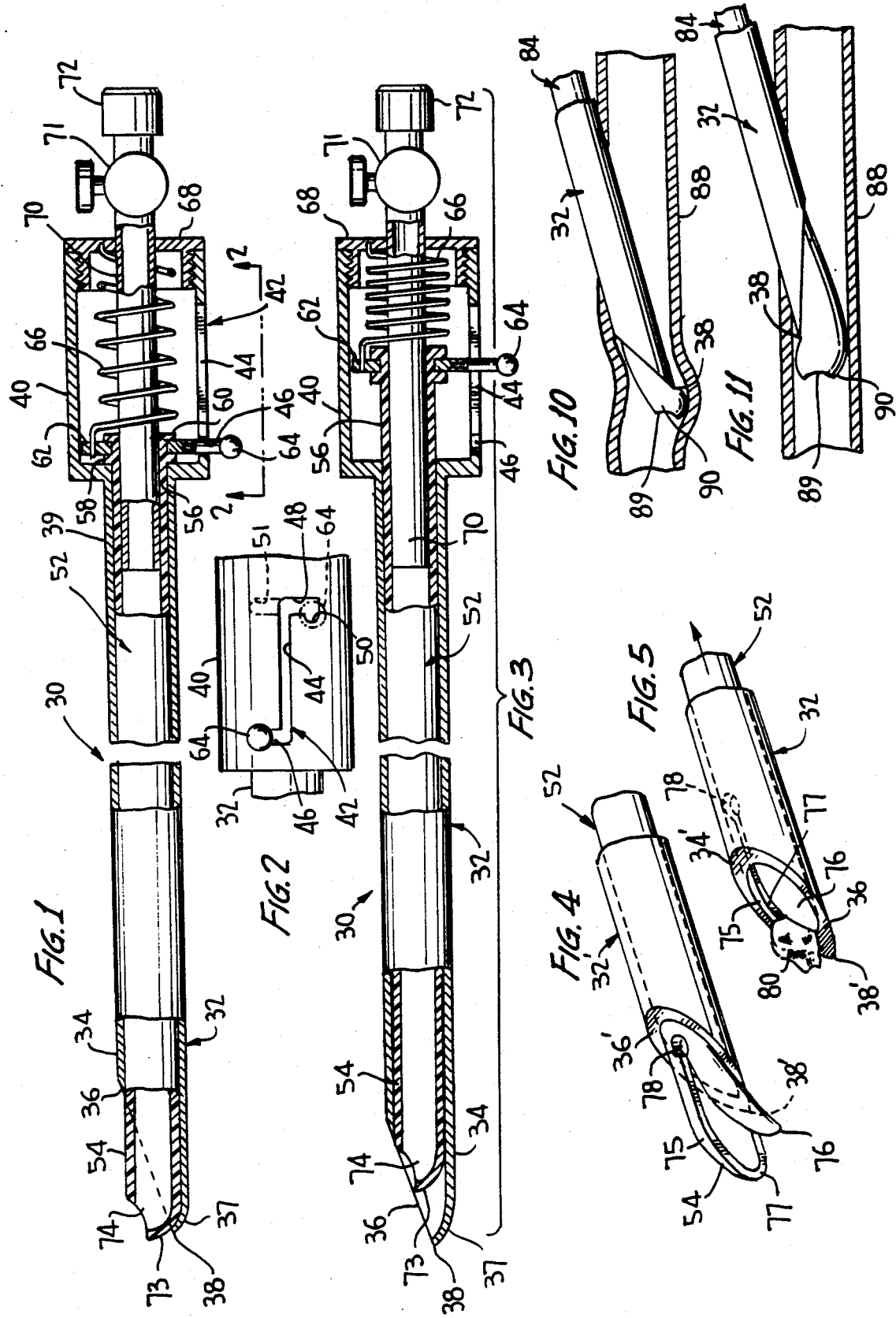

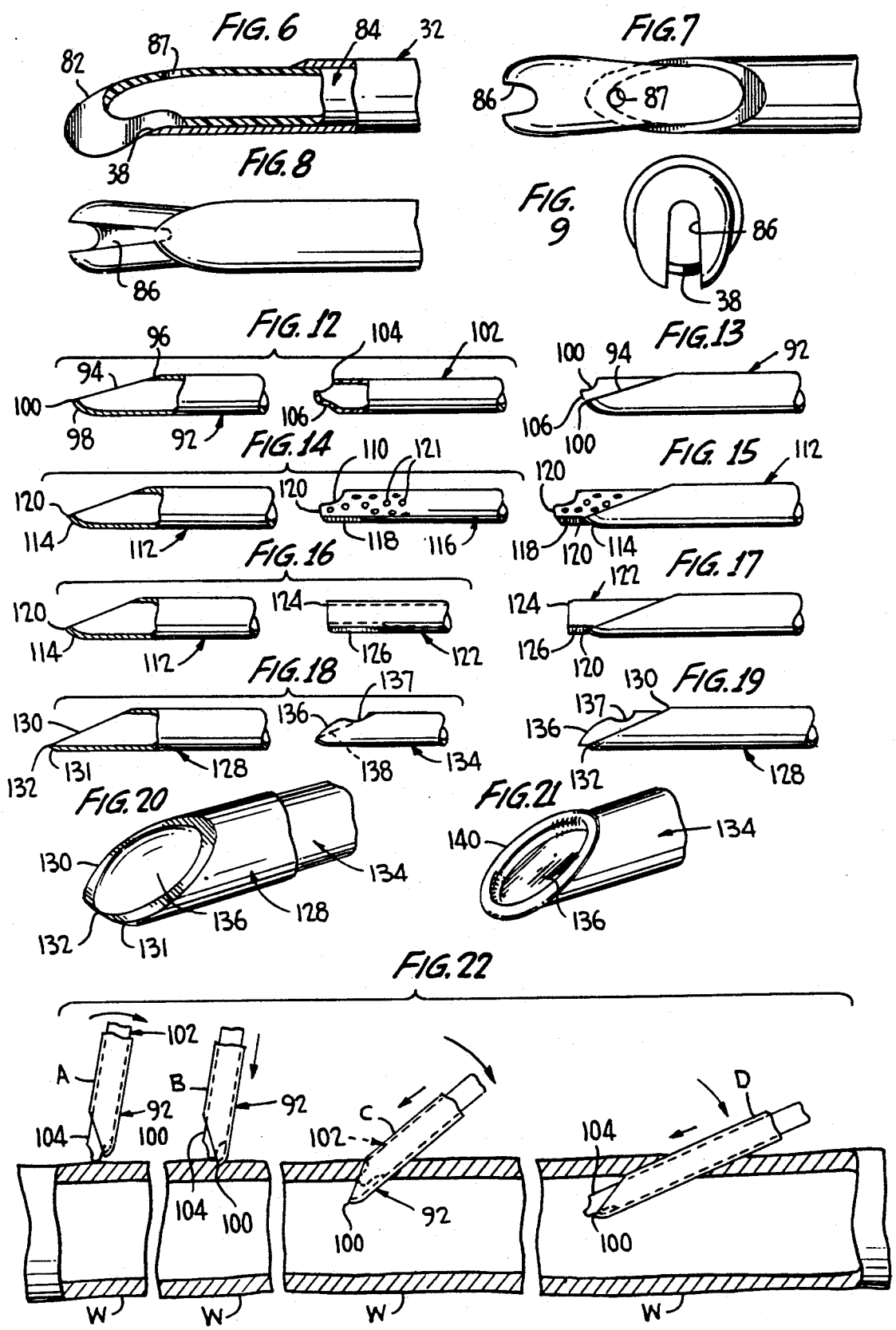

SAFETY NEEDLE

BACKGROUND OF THE INVENTION

1. Field of the Invention

The present invention pertains to safety penetrating instruments and, more particularly, to safety needles having protected sharp tips to prevent inadvertent tissue contact.

2. Discussion of the Prior Art

Penetrating instruments are widely used in surgical procedures to gain access to anatomical cavities ranging in size from the abdomen to small blood vessels, such as veins and arteries, epidural, pleural and subarachnoid spaces, heart ventricles and spinal synovial cavities Such surgical penetrating instruments include a penetrating member or implement having a sharp tip or point to pierce or penetrate the tissue forming the cavity wall, and the force required to penetrate the cavity wall is dependent upon the type and thickness of the tissue of the wall. Once the wall is penetrated, it is desirable to protect the sharp tip of the penetrating member to prevent inadvertent contact with tissue in the cavity, and a particular problem exists where substantial force is required to penetrate the cavity wall in that, once penetration is achieved, the lack of tissue resistance can result in the sharp tip travelling too far into the cavity and injuring adjacent tissue.

Safety penetrating instruments including a safety probe biased to extend beyond the sharp tip of the penetrating member have become widely accepted for use in penetrating anatomical cavities. For example, the Verres needle, commonly used to create a pneumoperitoneum, has a spring-loaded inner member disposed within a tubular needle. U.S Pat. Nos. 1,527,291 to Zorraquin, No. 2,623,521 to Shaw and No. 2,630,803 to Baran are exemplary of safety penetrating instruments with a spring-loaded inner member disposed in a needle, while U.S. Pat. No. 4,254,762 to Yoon shows an endoscope spring-biased in a hollow needle. Safety trocars having a spring-biased protective shield disposed between an outer sleeve and an inner trocar are marketed by Ethicon, Inc. as the Endopath and by United States Surgical Corp. as the Surgiport. U.S. Pat. Nos. 4,535,773 to Yoon and No. 4,654,030 to Moll et al are exemplary of such safety trocars. German Offenlegungsschrift 2,544,262 discloses an intrauterine catheter including a tube having a distal sharp point, a spring-biased blunt member in the tube distal end and a hose or catheter slidable over the tube.

While prior art safety penetrating instruments are widely used, they suffer from many disadvantages when used in the procedures for which they are presently recommended; and, additionally, prior art safety penetrating instruments cannot be used in many procedures for which safety of penetration is highly desirable. One of the disadvantages of prior art safety penetrating instruments is that, when the penetrating member is a tubular needle with an acutely angled distal end, the sharp tip is not well protected and is still at least partially exposed when the safety probe is in the protective extended position.

Other disadvantages of prior art safety needles are that the safety probe cannot be controlled to provide selective locking or retraction of the safety probe.

SUMMARY OF THE INVENTION

Accordingly, it is a primary object of the present invention to overcome the above mentioned disadvantages of the prior art and to provide safety needles with well protected tips for use in a wide range of surgical procedures thereby increasing safety and efficacy of the procedures.

Another object of the present invention is to receive the sharp tip of a tubular needle in a protective recess in a safety probe to minimize exposure of the sharp tip both after penetration of tissue and during handling by medical personnel thereby reducing the opportunity for contact and/or cutting of tissue inadvertently.

A further object of the present invention is to align an angled distal end surface of a safety probe with an angled sharp distal end of a tubular needle such that the distal ends of the safety probe and the needle are in substantially the same plane during tissue penetration to facilitate puncture.

An additional object of the present invention is to utilize a safety probe in a penetrating tubular needle having an open distal end with a portion curving toward the longitudinal axis of the needle to terminate at a sharp tip such that, in an extended position, the distal end of the safety probe protrudes over the sharp tip of the needle.

The present invention has another object in that a safety probe movable in an elongate, tubular needle is biased toward an extended position and can be selectively, releasably locked in a retracted position such that the safety probe can be disabled prior to or after puncture of a cavity wall.

Yet another object of the present invention is to construct a safety needle such that a distally biased safety probe can be manually pulled proximally toward a retracted position to expose the sharp distal tip of the needle without requiring a force applied to the distal end of the safety probe from tissue contact.

A further object of the present invention is to utilize a safety probe having an expandable distal end in a safety needle such that, in an extended position, the distal end of the safety probe is in an expanded state protecting the sharp tip of the needle while, in a retracted position, the distal end of the safety probe is in a contracted state substantially filling the needle distal end. The distal end of the safety probe can be slotted or split to permit further use for grasping and/or cutting tissue, such as for biopsy.

The present invention has an additional object in the use of a pin and slot mechanism to provide selective locking of a safety probe distally biased relative to a needle, the pin extending through the slot to be graspable by a surgeon to selectively move the safety probe within the needle. When the pin is in a longitudinal portion of the slot, the safety probe is free to move against the bias; and, when the pin is in proximal or distal transverse portions of the slot at opposite ends of the longitudinal portion, the safety probe is releasably locked in retracted and extended positions, respectively.

Some of the advantages of the present invention over the prior art are that very small cavities, such as veins, arteries, pleural spaces, spinal canals and subarachnoid and epidural spaces, can be safely penetrated, the chance of developing a hematoma during penetration of a vein or artery is substantially reduced, safety is much greater than with conventional Verres and Tuohey needles, safe penetration is achieved while permitting injection or evacuation of fluids, penetration into additional tissue after penetration of a cavity wall can be accomplished with a single instrument, such as into a cystic cavity or soft organ structure (e.g., ovarian cyst penetration or liver tissue biopsy), when used as an IV needle the receiving of the sharp tip in a protective recess in the safety probe increases safety both within and outside the body and decreases inadvertent contact and the concomitant trauma and spread of disease, and safety needles according to the present invention can be inexpensively manufactured to permit universal use in place of presently used tubular needles.

The present invention is generally characterized in a safety needle including an elongate, tubular needle and a safety probe movable therein between an extended position with a blunt distal end of the safety probe projecting distally of the distal end of the needle and a retracted position with the safety probe distal end disposed proximally of the distal end of the needle. In one embodiment, the safety probe forms a protective recess for receiving the sharp tip of the needle when the probe distal end is in the extended position In another embodiment, the distal end of a tubular needle has a peripheral edge disposed in a plane positioned at an acute angle relative to the longitudinal axis of the needle, and the safety probe has a distal end surface disposed in substantially the same plane as the distal end of the needle during penetration through tissue. In a further embodiment, the elongate, tubular needle has a distal end with a portion curving toward the longitudinal axis of the needle to terminate at a sharp leading tip, and the safety probe distal end is movable between an extended position with the safety probe distal end protruding over the needle tip and a retracted position with the safety probe distal end disposed proximally of the needle tip. An additional embodiment includes a pin and slot locking mechanism for selectively, releasably locking the safety probe in a retracted position or in an extended position. In another embodiment, the safety probe has a distal end having an expanded state in the extended position and a contracted state in the retracted position.

Other objects and advantages of the present invention will become apparent from the following description of the preferred embodiments taken in conjunction with the accompanying drawings wherein like parts in each of the several figures are identified by the same reference characters.

BRIEF DESCRIPTION OF THE DRAWINGS

FIG. 1 is a broken side view, partly in section, of a safety needle according to the present invention in an extended position FIG. 2 is a view of the hub and locking mechanism taken along line 2—2 of FIG. 1.

FIG. 3 is a broken side view, partly in section, of the safety penetrating instrument of FIG. 1 in a retracted position.

FIGS. 4 and 5 are broken perspective views of a modified safety needle according to the present invention;

FIG. 6 is a broken side view, partly in section, of another modification of a safety needle according to the present invention.

FIGS. 7, 8 and 9 are broken top, bottom and end views, respectively, of the safety needle of FIG. 6.

FIGS. 10 and 11 are broken views, partly in section, illustrating use of safety needles according to the present invention for penetrating narrow anatomical cavities.

FIG. 12 is a broken, exploded view of another embodiment of a safety needle according to the present invention.

FIG. 13 is a broken side view of the safety needle of FIG. 12 with the safety probe in an extended position.

FIG. 14 is a broken, exploded view of another embodiment of a safety needle according to the present invention.

FIG. 15 is a broken side view of the safety needle of FIG. 14 with the safety probe in an extended position.

FIG. 16 is a broken, exploded view of another embodiment of a safety needle according to the present invention.

FIG. 17 is a broken side view of the safety needle of FIG. 16 with the safety probe in an extended position FIG. 18 is a broken, exploded view of another embodiment of a safety needle according to the present invention.

FIG. 19 is a broken side view of the safety needle of FIG. 18 with the safety probe in an extended position.

FIG. 20 is a broken perspective view of the distal end of the embodiment of FIGS. 18 and 19.

FIG. 21 is a broken perspective view of the distal end of a modified safety probe for a safety needle according to the present invention.

FIG. 22 is a broken view, partly in section, illustrating use of the safety needle according to the present invention.

DESCRIPTION OF THE PREFERRED EMBODIMENTS

A safety needle 30 according to the present invention is illustrated in FIGS. 1, 2 and 3 and includes an elongate, tubular needle 32 preferably made of a cylindrical length of stainless steel having a diameter and wall thickness dependent upon the procedure to be formed and the anatomical cavity to be penetrated. The needle has a distal end 34 with an open end defining a peripheral edge 36 disposed in an acutely angled plane relative to the longitudinal axis of the needle and having a portion 37 curving toward the longitudinal axis of the needle to terminate at a sharp, tissue penetrating tip or point 38 radially, inwardly spaced from the cylindrical needle wall. Needle 32 has a proximal end 39 secured to a cylindrical hub 40 preferably made of plastic with the needle distal end threadedly or otherwise secured thereto; however, the needle and the hub can be formed either integrally or as separate components. As best shown in FIG. 2, the hub 40 has a slot 42 therein formed of a longitudinal portion 44 aligned in parallel relation with the longitudinal axis of needle 32, a distal transverse portion 46 and a proximal transverse portion 48. The portions 46 and 48 extend substantially transversely from longitudinal portion 48, and proximal transverse slot portion 48 has a recess 50 at the end thereof extending parallel with the longitudinal slot portion 44. If desired, the proximal slot portion can extend in the same direction as the distal slot portion as shown in phantom at 51.

An elongate, tubular safety probe 52 is slidably and concentrically disposed within needle 32 and is preferably made from a cylindrical length of a rigid or flexible material, such as stainless steel or plastic dependent upon use. The safety probe has a distal end 54 configured to protect needle tip 38 in an extended position and a proximal end 56 disposed within hub 40. Proximal end 56 has spaced annular ribs 58 and 60 between which is rotatably mounted a plate 62 to which is threadedly secured a pin 64 extending through slot 42 and having a spherical, knob-like end to be easily grasped. A helical spring 66 is mounted in compression between plate 62 and an end cap 68 threadedly mounted in the proximal end of hub 40. The spring 66 has longitudinally extending ends received in apertures in plate 62 and end cap 68 such that the spring 66 can be wound in torsion to bias the plate and the pin 64 carried thereby in a clockwise direction looking at the proximal end of the safety needle or upwardly looking at FIG. 2. End cap 68 has a longitudinally extending tube 70 secured centrally therein with a distal portion passing through hub 40 and into the tubular body of safety probe 52 and a proximal portion communicating with a stop cock 71 carrying a fitting 72 such that communication is established through the entirety of the safety needle 30. The distal end 54 of the safety probe has a configuration with a partially spherical, bulging, dome-like end surface 73 to protect the sharp point 38 of needle 32 as previously noted, and a hole 74 is disposed in the distal end to permit evacuation or injection of fluids through the safety needle. In order to assemble the safety needle 30, the safety probe 52 is inserted in the proximal end of hub 40 and through the needle. With the plate 62 in place, the pin 64 is passed through the slot 42 and screwed into the plate 62 such that the plate 62 can not rotate within the hub 40. Cap 68 is twisted clockwise to create torsion in the spring biasing plate 62 and pin 64 clockwise as noted above, and the cap 68 is then screwed into the threaded end of hub 40 to place the safety needle 30 in the condition illustrated in FIG. 1 wherein the distal end 54 of the safety probe 52 is normally in the extended position due to the bias of spring 66 toward the left looking at FIG. 1. The pin 64 will, accordingly, be biased distally along longitudinal portion 44 of slot 42; and since the spring 66 also provides a torsional bias, the pin will be biased clockwise into transverse slot portion 46 to releasably lock the safety probe in the extended position.

In use, it will be appreciated that with the pin 64 disposed in transverse slot portion 46, the safety probe cannot move proximally within needle 32 thereby assuring that the sharp tip 38, is protected to prevent inadvertent contact. When it is desired to penetrate an anatomical cavity, the blunt end surface 73 of safety probe distal end 54 is positioned in abutment with the tissue to be penetrated, and a finger is utilized to manually move pin 64 counter-clockwise against the torsional bias of spring 66 to be aligned with the longitudinal portion 44 of slot 42. With the pin 64 in this position, when the end surface 73 of distal end 54 is forced against the tissue to be penetrated, the safety probe 52 will move distally against the bias of spring 66 to a retracted position exposing the sharp tip 38 of the needle as illustrated in FIG. 3. In the retracted position of the safety probe where the distal end surface 73 is aligned just proximally of the needle peripheral edge 36 to expose the sharp tip 38, the pin 64 is disposed in longitudinal slot portion 44, as shown in FIG. 3, and is free to move longitudinally with or against the bias of spring 66. Transverse slot portion 48 is disposed proximally of the position of pin 64 in the retracted position illustrated in FIG. 3; however, if transverse slot portion 48 were aligned with pin 64, the pin would not enter the transverse slot portion 48 due to the torsional or rotational bias of spring 66 in the opposite direction. Thus, once the anatomical wall has been completely penetrated, spring 66 will bias the safety probe distally such that distal end 54 returns to the extended position illustrated in FIG. to protect the sharp tip 38 which is exposed only during the penetrating step.

If, after penetration into the anatomical cavity, the surgeon desires to penetrate additional tissue, the surgeon can selectively release the distal end of the safety probe from the extended position by again moving pin 64 counter-clockwise to be aligned . with longitudinal slot portion 44. If the protection provided by the safety probe 52 is not required or desired for further procedures, the pin 64 can be moved into recess 50 of transverse slot portion 48 to releasably lock the distal end of the safety probe in a retracted position. If slot portion 51 is provided, the safety probe will automatically lock in a retracted position when pin 64 is aligned with slot portion 51 due to the rotational bias from spring 66. If slot portion 51 is positioned proximally of pin 64 when the safety probe is in the retracted position shown in FIG. 3, the pin will have to be manually pulled back to alignment with slot portion 51 to lock the safety probe in a retracted position within the needle.

Once the safety needle has penetrated into an anatomical cavity, the safety needle can be used to permit flow of fluids into or out of the cavity since communication is established through the hole 74 and the body of the safety probe 52 and through tube 70 and valve 71. In this manner, the safety needle 30 can be used, for example, to create a pneumoperitoneum. If desired, the safety probe can be entirely withdrawn from the needle by unscrewing end cap 68 and pin 64 leaving the needle in place in the anatomical cavity.

A modification of the safety needle 30 is shown in FIG. 4 wherein the needle 32' has a distal end 34' formed like a conventional hypodermic needle to have an angled peripheral edge 36' defining a leading sharp tip 38' aligned with the outer surface of the cylindrical needle wall. The distal end 54 of the safety probe is split or slotted to form opposing parts 75 and 76. The split or slot 77 terminates at a radiused end 78 such that the parts 75 and 76 are biased away from each other to produce an expanded state when the safety probe is in the extended position. Additionally, the distal end 54 is bent or angled relative to the longitudinal axis of needle 32' such that, in the extended position, the bent portion of the safety probe distal end forms a concave recess receiving the sharp tip 38' of the needle. By constructing the safety probe of a flexible material, such as plastic, the bent or angled portion of distal end 54 will straighten out as the safety probe is withdrawn into the needle 32'; and, additionally, the distal end will be contracted such that parts 75 and 76 abut each other in the retracted position. When the safety probe returns to the extended position, the distal end will return to the bent or angled configuration forming a recess for receiving the needle tip. Thus, when the safety probe is in the extended position, the sharp tip 38' is protected by both the protective recess formed by slot 77 and the concave recess formed by bending or angling of the distal end 54. The angle or slope of the end surface of the distal end corresponds with the angle of needle distal end 34' such that the distal ends of the needle and the safety probe are disposed in substantially the same plane to reduce tissue resistance during penetrating and to produce a minimum gap between the safety probe and the needle to minimize trapping or jamming of tissue therebetween.

Use of the safety needle of FIG. 4 for grasping and/or cutting tissue, for example for biopsy, is illustrated in FIG. 5 wherein it can be seen that tissue 80 can be grasped by placing the safety probe adjacent the tissue in its expanded state as shown in FIG. 4 and, thereafter, pulling the safety probe proximally into the needle by manually grasping pin 64 and moving the pin along longitudinal slot portion 44 against the bias of spring 66. The safety probe can be releasably locked in the retracted position by moving the pin 64 into transverse slot portion 48 and into the recess 50 formed therein which prevents the pin from returning to its normally biased position, and the position of the transverse slot portion 48 along the longitudinal slot portion can be set to align the safety probe distal end at a desired locked retracted position relative to the needle distal end dependent upon the procedure and the tissue to be grasped or cut for biopsy. When the safety needle is used for biopsy, the safety probe is preferably made of stainless steel, and the inner edges of parts 75 and 76 are sharp to cut the tissue as the parts contract.

Another modification of safety needle 30 is illustrated in FIGS. 6, 7, 8 and 9 with the primary difference being the configuration of the distal end 82 of the safety probe 84. Distal end 82 has a groove or recess 86 formed therein such that the distal end is closed with the exception of a lateral hole 87 while still having a configuration to receive and protect the sharp tip 38' of needle 32', the tip being received in groove-like recess 86 as best shown in FIGS. 6 and 9 in the extended position. The distal end 82 is bent or angled relative to the longitudinal axis of needle 32' to additionally cover or surround the sharp needle tip 38'. The distal end of the safety probe is expanded in the extended position and contracts when withdrawn into the needle to the retracted position to substantially fill the needle distal end.

FIG. 10 illustrates use of the safety needle of the present invention to penetrate a narrow anatomical cavity, such as a blood vessel 88, and it should be appreciated from the drawing, that needle tip 38 is prevented from engaging the wall of blood vessel 88 due to the protruding blunt end surface of distal end 82 of the safety probe 84. The sharp point 38 is shown in a distalmost orientation relative to the surgical needle in FIG. 10 to align the needle open distal end with the blood vessel; and, in FIG. 11, the safety needle is illustrated for penetrating a blood vessel 88 wherein the sharp needle point 38 remains adjacent the wall punctured by the needle such that the needle open distal end faces transverse to the blood vessel. The distal end 90 of the safety probe illustrated in FIGS. 10 and 11 has a protective recess formed essentially by bending or angling a portion of the distal end without a groove therein, the angled portion forming a recess with the remaining body of the safety probe to receive and protect sharp point 38 as illustrated. Additionally, a hole 89 is formed in the distal end surface of the safety probe to align with the axis of the blood vessel.

Another embodiment of a safety needle according to the present invention is illustrated in FIG. 12 wherein a needle 92 is similar to needle 32 and has a distal end 94 with an open, acutely angled end defining a peripheral edge 96 with a portion 98 of distal end 94 curving toward the longitudinal axis of the needle 92 to terminate at a sharp tip 100. A safety probe 102 has a distal end 104 with a curvature to protrude over sharp tip 100 when the safety probe is in an extended position as illustrated in FIG. 13. The distal end 104 has a bulbous configuration with an aperture 110 therein to permit communication through the safety needle for injection or evacuation of fluid. Due to the curving portion 98 of the needle 92, the needle tip will be received in a protective recess or concavity 106 in safety probe distal end 104 to prevent exposure of the sharp tip.

Another embodiment of a safety needle according to the present invention is illustrated in FIGS. 14 and 15 wherein an elongate tubular needle 112 has a curved distal portion 114 extending less than portion 98 shown in FIG. 12. A safety probe 116 has a longitudinal groove 118 therein to form a recess receiving a sharp tip 120 at the distal end of the needle as illustrated in FIG. 15. The distal end of the safety probe has a plurality of small holes 121 therein and can also have an aperture 110 as illustrated in FIG. 12. By providing a plurality of holes in the distal end of the safety probe, communication can be maintained even if one of the holes becomes blocked.

The embodiment of a safety needle according to the present invention illustrated in FIG. 16 is similar to that illustrated in FIG. 14 with the exception that the safety probe 122 has an annular distal end 124 providing a completely open end allowing communication directly therethrough. The round peripheral edge of distal end 124 is interrupted to define a recess in the form of a slot or groove 126 for receiving the sharp point 120 of the needle.

The safety needle illustrated in FIGS. 18 and 19 includes a needle 128 similar to needle 32' in the embodiment of FIG. 4 with the exception that the leading point at the distal end 130 is ground or otherwise angled at 131 to terminate at sharp tip 132 aligned with the inner surface of the needle wall. The safety probe 134 has a distal end with a surface 136 disposed at an acute angle to the longitudinal axis of the needle substantially the same as the acute angle of the peripheral edge at the distal end 130 of needle 128. In this manner, the peripheral edge of the distal end of needle 128 and the distal end surface 136 of safety probe 134 will be maintained in substantially parallel relation in the extended position as illustrated in FIG. 19 and will be positioned in substantially the same plane in the retracted position as illustrated in FIG. 20. Accordingly, the safety needle illustrated in FIGS. 18 and 19 provides a smooth surface of minimal resistance to penetration of tissue. End surface 136 is shown as having a rounded, partially spherical or bulging, dome-shaped configuration; however, dependent upon use of the safety needle, the end surface can be flat as shown in phantom at 138. By grinding sharp tip 132 of the needle, the tip is positioned in abutment with the lateral wall of the safety probe to be protected without the use of a recess; however, a recess can be provided in the distal end of the safety probe as described above.

The distal ends of needle 128 and safety probe 134 are shown in FIG. 20 with the safety probe in the retracted position, and it can be seen therefrom that the distal ends are in substantially the same plane. Additionally, it can be seen that the angling of the distal end of the safety probe allows the open needle distal end to be substantially filled by the distal end of the safety probe such that gaps between the distal ends are minimized to reduce trapping or jamming of tissue between the needle and the safety probe. Where a particular use of the safety needle requires even further gap reduction, a protruding peripheral rim 140, as shown in FIG. 21, can be disposed around distal end surface 136 such that the rim expands laterally when the safety probe is in the extended position and contracts to fill the needle when the safety probe is in the retracted position.

Only the distal portions of the safety probes and needles have been illustrated in the safety needles shown in FIGS. 4 through 21; however, it will be appreciated that the proximal portions can be formed with any co-operating structure and are particularly advantageous when utilized with the locking and spring biasing mechanism illustrated in FIGS. 1, 2 and 3. Similarly, various features from the disclosed embodiments can be combined dependent upon the procedure to be performed with a particular safety needle.

The method of use of safety needles according to the present invention where the needle has a distal end with a portion curving toward the longitudinal axis, is illustrated in FIG. 22 with the embodiment of FIGS. 12 and 13. Use of the needle incorporates a rotating, scoop-like movement rather than a straight ahead penetration. The safety needle is initially placed against an anatomical wall W, such as that of a blood vessel, in the position shown at A such that the distal end 104 of the safety probe 102 contacts the wall W. The safety needle is then rotated clockwise such that the sharp point 100 of the needle initially penetrates the wall with the safety needle being forced transversely as illustrated at B and the safety probe moving proximally from the extended position to a retracted position exposing the needle tip. As penetration is achieved, the safety needle is rotated clockwise while being forced inwardly causing the safety probe to move further proximally within the needle, as shown at C. Once the safety needle has entered the anatomical cavity, the safety probe will move to the extended position in response to the spring bias. In this manner, the safety needle is rotated into the anatomical cavity facilitating precise penetration and positioning with reduced tissue compression.

From the above, it will be appreciated that safety needles according to the present invention provide increased protection of the sharp tip of the needle while also facilitating use and tip exposure after penetration of an anatomical cavity by providing selective, releasable locking positions for the safety probe. Safety probes having a distal end configured to define a protective recess for receiving the sharp tip of the needle in the extended position are particularly advantageous for safely puncturing veins or arteries with reduction of the chances of developing hematoma and can replace present IV needles. Safety of Tuohey-type needles, that is elongate tubular needles with an acutely angled distal end including a portion curving toward the longitudinal axis of the needle to terminate at a sharp tip radially, inwardly spaced from the wall of the needle, is increased with the use of safety probes having a distal end configured to protrude over the sharp tip in an extended position. Accordingly, rotational penetration can be safely performed to expand the use of Tuohey-type needles. The distal end portion of the needle can be curved inwardly to any desired extent from a slight curve to a curve through almost the entire diameter of the needle to produce a sharp, spoon-like shape with the distal end of the safety probe configured to protrude over the sharp tip by providing a protective recess therein or by bending in the same direction as the curvature of the curved portion.

If automatic locking of the safety probe 52 in the extended position is not desired, the spring 66 is not wound during assembly such that pin 64 is not rotationally biased. Accordingly, after spring 66 returns the safety probe 52 to the extended position when the force on the safety probe distal end from tissue resistance is removed, the pin will not enter transverse portion 46, and the safety probe will not be locked in the extended position. Thus, the surgeon has the option of locking the safety probe in the extended position by manually moving pin 64 into transverse slot portion 46 or allowing the safety probe to be free to move proximally by not moving pin 64 into transverse slot portion 46.

While plate 62 and pin 64 can rotate slightly within hub 38, safety probe 34 does not rotate therewith thereby maintaining alignment of the safety probe with needle 32, and various index configurations to maintain rotational alignment between the safety probe and the needle can be used, if desired. For example, the safety probe can be splined with the needle or with tube 70.

The safety needle of the present invention can be used for penetrating various types of tissue and anatomical cavities and can have various diameters ranging from 2mm to 12mm. When the safety probe includes a protective recess, such as a bent or angled portion, a slot, a groove or a concavity, the sharp needle tip is protected by being received in the recess. As previously noted, when the angle of the end surface of the safety probe distal end corresponds with the angle of the needle distal end, the distal ends of the needle and the safety probe will be disposed in substantially the same plane to reduce tissue resistance during penetrating and produce a minimum gap between the safety probe and the needle to minimize trapping or jamming of tissue therebetween. Protection of the sharp needle tip is particularly effective where the distal end of the needle is ground as shown at 131 in that the sharp needle tip will be aligned with the wall of the distal end of the safety probe when the safety probe is in the extended position. Dependent upon the configuration of the safety probe to be used and the procedure to be performed, the safety probe can be made of metal, such as stainless steel, rubber or plastic, with materials having good sliding characteristics, such as Teflon, being preferred. The use of a flexible or resilient material is preferred for the safety probes having bent or angled distal end portions to facilitate straightening out for alignment in the needle in the retracted position; however, metal such as stainless steel is preferred for the embodiment of FIGS. 4 and 5 when used to cut tissue for biopsy. While the needles can be made of any suitable material, stainless steel is preferred. The safety probes are advantageously hollow or tubular to allow passage of fluids therethrough; however, the safety probes can be solid if desired.

From the above it will be appreciated that safety needles according to the present invention provide increased protection of the sharp tip of a tubular needle while also facilitating use and tip exposure after penetration of an anatomical cavity by providing selective, releasable locking of the safety probe. The safety needles of the present invention are useful to penetrate tissue in various portions of the body, and "anatomical cavity" as used herein refers to any area of the body requiring penetration of tissue for access.

Inasmuch as the present invention is subject to many variations, modifications and changes in detail, it is intended that all subject matter discussed above or shown in the accompanying drawings be interpreted as illustrative only and not to be taken in a limiting sense.

What is claimed is:

1. A safety needle comprising an elongate, tubular needle having a longitudinal axis and an open distal end defining a sharp leading tip for penetrating tissue;
   a safety probe movably disposed in said needle and having a distal end movable between an extended position with said probe distal end protruding distally from said needle tip and a retracted position with said probe distal end disposed proximally of said needle tip; and
   means biasing said safety probe toward said extended position,
   said safety probe being formed by a tubular member terminating proximally at a proximal end engaged by said biasing means and terminating distally at said probe distal end, said probe distal end having a blunt end surface and a tubular portion terminating at said blunt end surface and disposed at an angle relative to said needle longitudinal axis when said safety probe is in said extended position, said angled tubular portion forming a concave protective recess receiving said needle tip when said safety probe is in said extended position.

2. A safety needle as recited in claim 1 wherein said angled tubular portion of said probe is straightened to be aligned with said needle longitudinal axis when said safety probe is in said retracted position.

3. A safety needle comprising
   an elongate, tubular needle having a longitudinal axis and an open distal end with a portion curving toward said longitudinal axis to terminate at a sharp leading tip for penetrating tissue;
   a safety probe movably disposed in said needle and having a distal end movable between an extended position with said probe distal end protruding over said needle tip and a retracted position with said probe distal end disposed proximally of said needle tip; and
   means biasing said probe toward said extended position,
   said probe distal end including a protective recess receiving said needle tip when said safety probe is in said extended position.

4. A safety needle comprising an elongate tubular needle having a sharp distal end for penetrating tissue and a proximal end;
   a safety probe having a blunt distal end and movable within said needle between an extended position with said probe distal end protruding distally of said needle distal end and a retracted position with said probe distal end disposed proximally of said needle distal end;
   means for biasing said safety probe distally toward said extended position and for permitting said safety probe to move proximally to said retracted position in response to a proximally directed force applied to said probe distal end; and
   means responsive to said biasing means for automatically, releasably locking said safety probe in said extended position after puncturing of the wall of an anatomical cavity including means extending from said safety probe for permitting said safety probe to be pulled back to said retracted position.

5. A safety needle as recited in claim 4 wherein said locking means includes slot means and said extending means includes pin means received in said slot means.

6. A safety needle as recited in claim 5 wherein said slot means includes a longitudinal portion allowing movement of said pin means along the longitudinal axis of said needle and a transverse portion preventing movement of said pin means along said needle for selectively, releasably locking said safety probe in said extended position.

7. A safety needle as recited in claim 6 wherein said pin means is carried by said safety probe and said slot means is carried by said needle.

8. A safety needle comprising
   an elongate, tubular needle having a sharp distal end for penetrating tissue and a proximal end;
   a safety probe having a blunt distal end and movable within said needle between an extended position with said safety probe distal end protruding distally of said needle distal end and a retracted position with said probe distal end disposed proximally of said needle distal end;
   means for biasing said safety probe distally toward said extended position and for permitting said protective probe to move proximally to said retracted position in response to a proximally directed force applied to said probe distal end; and
   means for locking said safety probe in said extended position prior to penetrating tissue and requiring manual release simultaneously with a force moving said safety probe toward said retracted position, said locking means including a pin carried by said safety probe, a slot carried by said needle and receiving said pin and spring means biasing said pin to a locked position in said slot.

9. A safety needle as recited in claim 8 wherein said slot includes a longitudinal portion allowing movement of said pin along the longitudinal axis of said needle and a transverse portion preventing proximal movement of said pin along said needle for selectively, releasably locking said safety probe in said extended position, said pin being manually movable out of said transverse portion against the bias of said spring means to permit movement of said safety probe toward said retracted position.

* * * * *